United States Patent
Xu et al.

(10) Patent No.: US 12,239,699 B2
(45) Date of Patent: Mar. 4, 2025

(54) IMMUNOGEN FOR BROAD-SPECTRUM INFLUENZA VACCINE AND APPLICATION THEREOF

(71) Applicant: Shanghai Public Health Clinical Center, Shanghai (CN)

(72) Inventors: Jianqing Xu, Shanghai (CN); Xiaoyan Zhang, Shanghai (CN); Xinci Xie, Shanghai (CN)

(73) Assignee: Shanghai Public Health Clinical Center, Shanghai (CN)

( * ) Notice: Subject to any disclaimer, the term of this patent is extended or adjusted under 35 U.S.C. 154(b) by 911 days.

(21) Appl. No.: 17/275,253

(22) PCT Filed: Sep. 11, 2018

(86) PCT No.: PCT/CN2018/105020
§ 371 (c)(1),
(2) Date: May 7, 2021

(87) PCT Pub. No.: WO2020/051766
PCT Pub. Date: Mar. 19, 2020

(65) Prior Publication Data
US 2022/0118077 A1    Apr. 21, 2022

(51) Int. Cl.
| | |
|---|---|
| *A61K 39/145* | (2006.01) |
| *A61K 39/275* | (2006.01) |
| *A61P 31/16* | (2006.01) |
| *C07K 14/005* | (2006.01) |
| *C12N 7/00* | (2006.01) |
| *C12N 15/86* | (2006.01) |
| *A61K 39/00* | (2006.01) |

(52) U.S. Cl.
CPC .......... *A61K 39/145* (2013.01); *A61K 39/275* (2013.01); *A61P 31/16* (2018.01); *C07K 14/005* (2013.01); *C12N 7/00* (2013.01); *C12N 15/86* (2013.01); *A61K 2039/543* (2013.01); *A61K 2039/545* (2013.01); *C12N 2710/10043* (2013.01); *C12N 2710/10343* (2013.01); *C12N 2710/24134* (2013.01); *C12N 2760/16122* (2013.01); *C12N 2760/16134* (2013.01); *C12N 2800/00* (2013.01)

(58) Field of Classification Search
CPC ........ A61K 39/145; A61P 31/16; C12N 15/86
See application file for complete search history.

(56) References Cited

U.S. PATENT DOCUMENTS

| | | | | |
|---|---|---|---|---|
| 7,537,768 | B2 * | 5/2009 | Luke ...................... | A61P 31/16 435/235.1 |
| 9,708,585 | B2 * | 7/2017 | Mason .................. | A61K 39/145 |
| 2018/0245052 | A1 | 8/2018 | Egorov et al. | |

FOREIGN PATENT DOCUMENTS

| | | |
|---|---|---|
| CN | 101716340 A | 6/2010 |
| JP | 2014-513067 A | 5/2014 |
| WO | 2008/039267 A2 | 4/2008 |
| WO | 2009/016639 A2 | 2/2009 |
| WO | 2012/129295 A1 | 9/2012 |
| WO | 2017/078577 A1 | 5/2017 |

OTHER PUBLICATIONS

Office Action dated Dec. 6, 2022, issued in corresponding Japanese Patent Application No. 2021-513962.
Extended European Search Report issued in corresponding European Patent Application No. 18933057.4 dated Mar. 29, 2022.
Atsmon et al., "Safety and Immunogenicity of Multimeric-001-a Novel Universal Influenza Vaccine," Journal of Clinical Immunology, 32: 595-603 (2012).
Goodman et al., "A Human Multi-Epitope Recombinant Vaccinia Virus as a Universal T Cell Vaccine Candidate against Influenza Virus," PLOS One, 6 (10): e25938 (2011).
Xie et al., "Influenza Vaccine with Consensus Internal Antigens as Immunogens Provides Cross-Group Protection Against Influenza A Viruses," Frontiers in Microbiology, 10: 1630 (2019).
Office Action issued in corresponding Japanese Patent Application No. 2023-061353 dated Jun. 4, 2024.

* cited by examiner

*Primary Examiner* — Bao Q Li
(74) *Attorney, Agent, or Firm* — Morgan, Lewis & Bockius LLP

(57) ABSTRACT

The present disclosure relates to a novel influenza immunogen with broad-spectrum anti-influenza virus effect and the immunization method thereof. The present disclosure provides a novel anti-influenza immunogen whose sequence comprises the amino acid sequence shown in SEQ ID No: 1 and SEQ ID No: 2, or an immunogenic fragment thereof, or a combination thereof. In addition, the present disclosure also provides use of the recombinant vector vaccine using said immunogen in the anti-influenza vaccine, and the immunization method of the recombinant vector vaccine using said immunogen. Through the sequential administration of multiple vector vaccines expressing the novel influenza immunogen, and the combined use of systemic administration and local administration, a high-level T cell immune response is induced in the local respiratory tract, which can produce broad-spectrum protection against multiple influenza virus infections.

4 Claims, 6 Drawing Sheets

Figure 1:
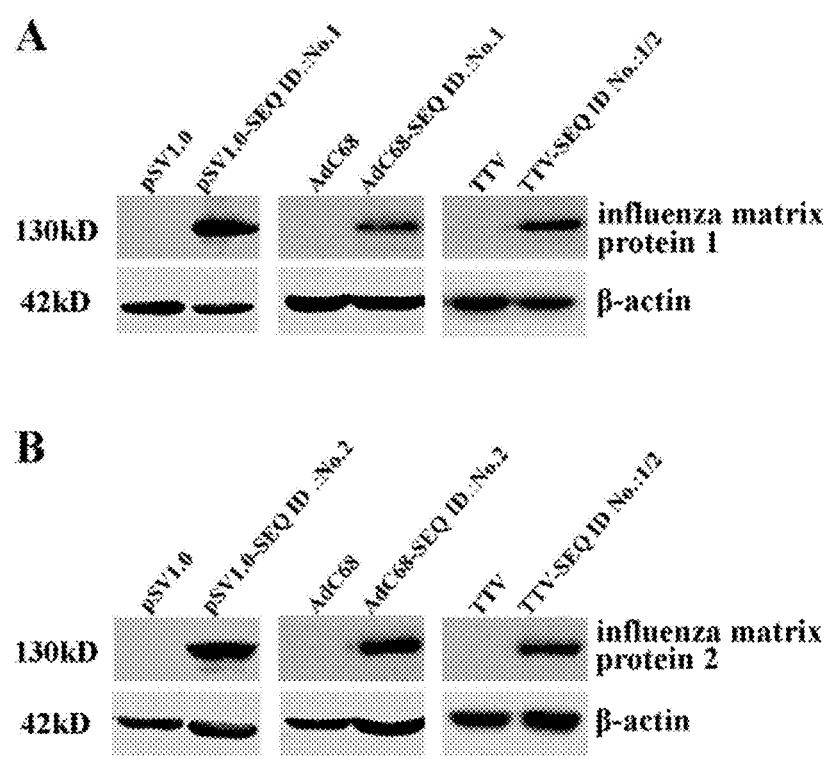

Specification includes a Sequence Listing.

SEQUENCE LISTING

```
<160> NUMBER OF SEQ ID NOS: 2

<210> SEQ ID NO 1
<211> LENGTH: 1169
<212> TYPE: PRT
<213> ORGANISM: Artificial Sequence
<220> FEATURE:
<223> OTHER INFORMATION: Synthetic Sequence

<400> SEQUENCE: 1

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Lys Trp Met Met Ala Met Lys Tyr Pro Ile Thr
        35                  40                  45

Ala Asp Lys Arg Ile Thr Glu Met Ile Pro Glu Arg Asn Glu Gln Gly
    50                  55                  60

Gln Thr Leu Trp Ser Lys Met Asn Asp Ala Gly Ser Asp Arg Val Met
65                  70                  75                  80

Val Ser Pro Leu Ala Val Thr Trp Trp Asn Arg Asn Gly Pro Val Thr
                85                  90                  95

Ser Thr Val His Tyr Pro Lys Val Tyr Lys Thr Tyr Phe Glu Lys Val
            100                 105                 110

Glu Arg Leu Lys His Gly Thr Phe Gly Pro Val His Phe Arg Asn Gln
        115                 120                 125

Val Lys Gln Leu Thr Ile Thr Lys Glu Lys Lys Glu Glu Leu Gln Asp
    130                 135                 140

Cys Lys Ile Ser Pro Leu Met Val Ala Tyr Met Leu Glu Arg Glu Leu
145                 150                 155                 160

Val Arg Lys Thr Arg Phe Leu Pro Val Ala Gly Gly Thr Ser Ser Val
                165                 170                 175

Tyr Ile Glu Val Leu Ile Val Arg Arg Ala Ala Val Ser Ala Asp Pro
            180                 185                 190

Leu Ala Ser Leu Leu Glu Met Cys His Ser Gly Leu Arg Ile Ser Ser
        195                 200                 205

Ser Phe Ser Phe Gly Gly Phe Thr Phe Lys Arg Thr Ser Gly Ser Ser
    210                 215                 220

Val Lys Lys Glu Glu Glu Val Leu Thr Gly Asn Leu Gln Thr Leu Lys
225                 230                 235                 240

Ile Arg Ile Val Ser Gly Arg Asp Glu Gln Ser Ile Ala Glu Ala Ile
                245                 250                 255

Ile Val Ala Met Val Phe Ser Pro Met His Gln Leu Leu Arg His Phe
            260                 265                 270

Gln Lys Asp Ala Lys Val Leu Phe Gln Asn Trp Gly Ile Glu His Ile
        275                 280                 285

Asp Asn Val Met Gly Met Ile Gly Ile Leu Pro Asp Met Thr Pro Ser
    290                 295                 300
```

```
Thr Glu Met Ser Val Ser Ile Asp Arg Phe Leu Arg Val Arg Asp Gln
305                 310                 315                 320

Arg Gly Asn Val Leu Leu Ser Pro Glu Glu Val Ser Glu Thr Gln Gly
            325                 330                 335

Thr Glu Lys Leu Thr Ile Thr Tyr Ser Ser Ser Met Met Trp Glu Ile
        340                 345                 350

Asn Gly Pro Glu Ser Val Leu Val Asn Thr Tyr Gln Trp Ile Ile Arg
    355                 360                 365

Asn Trp Glu Ala Val Lys Ile Gln Trp Ser Gln Asn Pro Thr Met Leu
370                 375                 380

Tyr Asn Lys Met Glu Phe Glu Pro Phe Gln Ser Leu Val Pro Lys Ala
385                 390                 395                 400

Ile Arg Ser Gln Tyr Ser Gly Phe Val Arg Thr Leu Phe Gln Gln Met
                405                 410                 415

Arg Asp Val Leu Gly Thr Phe Asp Thr Thr Gln Ile Ile Lys Leu Leu
            420                 425                 430

Pro Phe Ala Ala Ala Pro Pro Lys Gln Ser Arg Met Gln Phe Ser Ser
        435                 440                 445

Leu Thr Val Asn Val Arg Gly Ser Gly Met Arg Ile Leu Val Arg Gly
    450                 455                 460

Asn Ser Pro Val Phe Asn Tyr Asn Lys Thr Thr Lys Arg Leu Thr Val
465                 470                 475                 480

Leu Gly Lys Asp Ala Gly Thr Leu Thr Glu Asp Pro Asp Glu Gly Thr
                485                 490                 495

Ser Gly Val Glu Ser Ala Val Leu Arg Gly Phe Leu Ile Leu Gly Lys
            500                 505                 510

Glu Asp Arg Arg Tyr Gly Pro Ala Leu Ser Ile Asn Glu Leu Ser Val
        515                 520                 525

Met Lys Arg Lys Arg Asp Ser Ser Ile Leu Thr Asp Ser Gln Thr Ala
    530                 535                 540

Thr Lys Arg Ile Arg Met Ala Ile Asn Gly Ser Gly Gly Ser Gly Met
545                 550                 555                 560

Ala Ser Gln Gly Thr Lys Arg Ser Tyr Glu Gln Met Glu Thr Asp Gly
                565                 570                 575

Glu Arg Gln Asn Ala Thr Glu Ile Arg Ala Ser Val Gly Arg Met Ile
            580                 585                 590

Gly Gly Ile Gly Arg Phe Tyr Ile Gln Met Cys Thr Glu Leu Lys Leu
        595                 600                 605

Ser Asp Tyr Glu Gly Arg Leu Ile Gln Asn Ser Leu Thr Ile Glu Arg
    610                 615                 620

Met Val Leu Ser Ala Phe Asp Glu Arg Arg Asn Lys Tyr Leu Glu Glu
625                 630                 635                 640

His Pro Ser Ala Gly Lys Asp Pro Lys Lys Thr Gly Gly Pro Ile Tyr
                645                 650                 655

Arg Arg Val Asp Gly Lys Trp Met Arg Glu Leu Val Leu Tyr Asp Lys
            660                 665                 670

Glu Glu Ile Arg Arg Ile Trp Arg Gln Ala Asn Asn Gly Glu Asp Ala
        675                 680                 685

Thr Ala Gly Leu Thr His Ile Met Ile Trp His Ser Asn Leu Asn Asp
    690                 695                 700

Ala Thr Tyr Gln Arg Thr Arg Ala Leu Val Arg Thr Gly Met Asp Pro
705                 710                 715                 720
```

-continued

```
Arg Met Cys Ser Leu Met Gln Gly Ser Thr Leu Pro Arg Arg Ser Gly
                725                 730                 735

Ala Ala Gly Ala Ala Val Lys Gly Val Gly Thr Met Val Met Glu Leu
            740                 745                 750

Ile Arg Met Ile Lys Arg Gly Ile Asn Asp Arg Asn Phe Trp Arg Gly
        755                 760                 765

Glu Asn Gly Arg Lys Thr Arg Val Ala Tyr Glu Arg Met Cys Asn Ile
    770                 775                 780

Leu Lys Gly Lys Phe Gln Thr Ala Ala Gln Arg Ala Met Met Asp Gln
785                 790                 795                 800

Val Arg Glu Ser Arg Asn Pro Gly Asn Ala Glu Ile Glu Asp Leu Ile
                805                 810                 815

Phe Leu Ala Arg Ser Ala Leu Ile Leu Arg Gly Ser Val Ala His Lys
            820                 825                 830

Ser Cys Leu Pro Ala Cys Val Tyr Gly Pro Ala Val Ala Ser Gly Tyr
        835                 840                 845

Asp Phe Glu Lys Glu Gly Tyr Ser Leu Val Gly Ile Asp Pro Phe Lys
    850                 855                 860

Leu Leu Gln Asn Ser Gln Val Tyr Ser Leu Ile Arg Pro Asn Glu Asn
865                 870                 875                 880

Pro Ala His Lys Ser Gln Leu Val Trp Met Ala Cys His Ser Ala Ala
                885                 890                 895

Phe Glu Asp Leu Arg Val Ser Ser Phe Ile Arg Gly Thr Lys Val Ile
            900                 905                 910

Pro Arg Gly Lys Leu Ser Thr Arg Gly Val Gln Ile Ala Ser Asn Glu
        915                 920                 925

Asn Met Asp Thr Met Asp Ser Ser Thr Leu Glu Leu Arg Ser Arg Tyr
    930                 935                 940

Trp Ala Ile Arg Thr Arg Ser Gly Gly Asn Thr Asn Gln Gln Arg Ala
945                 950                 955                 960

Ser Ala Gly Gln Ile Ser Val Gln Pro Thr Phe Ser Val Gln Arg Asn
                965                 970                 975

Leu Pro Phe Glu Lys Ser Thr Val Met Ala Ala Phe Thr Gly Asn Thr
            980                 985                 990

Glu Gly Arg Thr Ser Asp Met Arg Ala Glu Ile Ile Arg Met Met Glu
        995                 1000                1005

Ser Ala Lys Pro Glu Glu Val Ser Phe Gln Gly Arg Gly Val Phe
        1010                1015                1020

Glu Leu Ser Asp Glu Lys Ala Thr Asn Pro Ile Val Pro Ser Phe
        1025                1030                1035

Asp Met Ser Asn Glu Gly Ser Tyr Phe Phe Gly Asp Asn Ala Glu
        1040                1045                1050

Glu Tyr Asp Asn Gly Gly Gly Ser Gly Gly Gly Ser Gly
        1055                1060                1065

Gly Gly Gly Ser Met Ser Leu Leu Thr Glu Val Glu Thr Pro Ile
        1070                1075                1080

Arg Asn Glu Trp Gly Cys Arg Cys Asn Asp Ser Ser Asp Pro Leu
        1085                1090                1095

Val Val Ala Ala Asn Ile Ile Gly Ile Leu His Leu Ile Leu Trp
        1100                1105                1110

Ile Leu Asp Arg Leu Phe Phe Lys Cys Ile Tyr Arg Leu Phe Lys
        1115                1120                1125

His Gly Leu Lys Arg Gly Pro Ser Thr Glu Gly Val Pro Glu Ser
```

```
                    1130                1135                1140
Met Arg Glu Glu Tyr Arg Lys Glu Gln Gln Asn Ala Val Asp Ala
        1145                1150                1155

Asp Asp Ser His Phe Val Ser Ile Glu Leu Glu
        1160                1165

<210> SEQ ID NO 2
<211> LENGTH: 1147
<212> TYPE: PRT
<213> ORGANISM: Artificial Sequence
<220> FEATURE:
<223> OTHER INFORMATION: Synthetic Sequence

<400> SEQUENCE: 2

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln His Phe Gln Arg Lys Arg Val Arg Asp Asn Met
                85                  90                  95

Thr Lys Lys Met Val Thr Gln Arg Thr Ile Gly Lys Lys Lys Gln Arg
                100                 105                 110

Leu Asn Lys Arg Gly Tyr Leu Ile Arg Ala Leu Thr Leu Asn Thr Met
            115                 120                 125

Thr Lys Asp Ala Glu Arg Gly Lys Leu Lys Arg Arg Ala Ile Ala Thr
    130                 135                 140

Pro Gly Met Gln Ile Arg Gly Phe Val Tyr Phe Val Glu Thr Leu Ala
145                 150                 155                 160

Arg Ser Ile Cys Glu Lys Leu Glu Gln Ser Gly Leu Pro Val Gly Gly
                165                 170                 175

Asn Glu Lys Lys Ala Lys Leu Ala Asn Val Val Arg Lys Met Met Thr
            180                 185                 190

Asn Ser Gln Asp Thr Glu Ile Ser Phe Thr Ile Thr Gly Asp Asn Thr
        195                 200                 205

Lys Trp Asn Glu Asn Gln Asn Pro Arg Met Phe Leu Ala Met Ile Thr
    210                 215                 220

Tyr Ile Thr Lys Asn Gln Pro Glu Trp Phe Arg Asn Ile Leu Ser Ile
225                 230                 235                 240

Ala Pro Ile Met Phe Ser Asn Lys Met Ala Arg Leu Gly Lys Gly Tyr
                245                 250                 255

Met Phe Glu Ser Lys Arg Met Lys Leu Arg Thr Gln Ile Pro Ala Glu
            260                 265                 270

Met Leu Ala Ser Ile Asp Leu Lys Tyr Phe Asn Glu Ser Thr Lys Lys
        275                 280                 285

Lys Ile Glu Lys Ile Arg Pro Leu Leu Ile Asp Gly Thr Ala Ser Leu
    290                 295                 300

Ser Pro Gly Met Met Met Gly Met Phe Asn Met Leu Ser Thr Val Leu
305                 310                 315                 320

Gly Val Ser Ile Leu Asn Leu Gly Gln Lys Lys Tyr Thr Lys Thr Thr
```

-continued

```
                325                 330                 335
Tyr Trp Trp Asp Gly Leu Gln Ser Ser Asp Phe Ala Leu Ile Val
            340                 345                 350
Asn Ala Pro Asn His Glu Gly Ile Gln Ala Gly Val Asp Arg Phe Tyr
            355                 360                 365
Arg Thr Cys Lys Leu Val Gly Ile Asn Met Ser Lys Lys Ser Tyr
            370                 375             380
Ile Asn Lys Thr Gly Thr Phe Glu Phe Thr Ser Phe Phe Tyr Arg Tyr
385                 390                 395                 400
Gly Phe Val Ala Asn Phe Ser Met Glu Leu Pro Ser Phe Gly Val Ser
                405                 410                 415
Gly Val Asn Glu Ser Ala Asp Met Ser Ile Gly Val Thr Val Ile Lys
            420                 425                 430
Asn Asn Met Ile Asn Asn Asp Leu Gly Pro Ala Thr Ala Gln Met Ala
            435                 440                 445
Leu Gln Leu Phe Ile Lys Asp Tyr Arg Tyr Thr Tyr Arg Cys His Arg
    450                 455                 460
Gly Asp Thr Gln Ile Gln Thr Arg Arg Ser Phe Glu Leu Lys Lys Leu
465                 470                 475                 480
Trp Asp Gln Thr Gln Ser Lys Ala Gly Leu Leu Val Ser Asp Gly Gly
                485                 490                 495
Pro Asn Leu Tyr Asn Ile Arg Asn Leu His Ile Pro Glu Val Cys Leu
                500                 505                 510
Lys Trp Glu Leu Met Asp Glu Asp Tyr Arg Gly Arg Leu Cys Asn Pro
            515                 520                 525
Leu Asn Pro Phe Val Ser His Lys Glu Ile Glu Ser Val Asn Asn Ala
    530                 535                 540
Val Val Met Pro Ala His Gly Pro Ala Lys Ser Met Glu Tyr Asp Ala
545                 550                 555                 560
Val Ala Thr Thr His Ser Trp Ile Pro Lys Arg Asn Arg Ser Ile Leu
                565                 570                 575
Asn Thr Ser Gln Arg Gly Ile Leu Glu Asp Glu Gln Met Tyr Gln Lys
            580                 585                 590
Cys Cys Asn Leu Phe Glu Lys Phe Pro Ser Ser Ser Tyr Arg Arg
            595                 600                 605
Pro Val Gly Ile Ser Ser Met Val Glu Ala Met Val Ser Arg Ala Arg
            610                 615                 620
Ile Asp Ala Arg Ile Asp Phe Glu Ser Gly Arg Ile Lys Lys Glu Glu
625                 630                 635                 640
Phe Ser Glu Ile Met Lys Ile Cys Ser Thr Ile Glu Glu Leu Arg Arg
                645                 650                 655
Gln Lys Gly Gly Gly Gly Ser Gly Gly Gly Ser Gly Gly Gly Gly
            660                 665                 670
Ser Met Arg Arg Asn Tyr Phe Thr Ala Glu Val Ser His Cys Arg Ala
            675                 680                 685
Thr Glu Tyr Ile Met Lys Gly Val Tyr Ile Asn Thr Ala Leu Leu Asn
    690                 695                 700
Ala Ser Cys Ala Ala Met Asp Asp Phe Gln Leu Ile Pro Met Ile Ser
705                 710                 715                 720
Lys Cys Arg Thr Lys Glu Gly Arg Arg Lys Thr Asn Leu Tyr Gly Phe
            725                 730                 735
Ile Ile Lys Gly Arg Ser His Leu Arg Asn Asp Thr Asp Val Val Asn
            740                 745                 750
```

```
Phe Val Ser Met Glu Phe Ser Leu Thr Asp Pro Arg Leu Glu Met Phe
        755                 760                 765

Leu Tyr Val Arg Thr Asn Gly Thr Ser Lys Ile Lys Met Lys Trp Gly
        770                 775                 780

Met Glu Met Arg Arg Cys Leu Leu Gln Ser Leu Gln Gln Ile Glu Ser
785                 790                 795                 800

Met Ile Glu Ala Glu Ser Ser Val Lys Glu Lys Asp Met Thr Lys Glu
                805                 810                 815

Phe Phe Glu Asn Lys Ser Glu Thr Trp Pro Ile Gly Glu Ser Pro Lys
                820                 825                 830

Gly Val Glu Glu Gly Ser Ile Gly Lys Val Cys Arg Thr Leu Leu Ala
                835                 840                 845

Lys Ser Val Phe Asn Phe Asp Leu Gly Gly Leu Tyr Glu Ala Ile Glu
        850                 855                 860

Glu Cys Leu Ile Asn Asp Pro Trp Val Leu Leu Asn Ala Ser Trp Phe
865                 870                 875                 880

Asn Ser Phe Leu Thr His Ala Leu Lys Gly Ser Gly Ser Gly Ser Met
                885                 890                 895

Ser Leu Leu Thr Glu Val Glu Thr Tyr Val Leu Ser Ile Val Pro Ser
        900                 905                 910

Gly Pro Leu Lys Ala Glu Ile Ala Gln Arg Leu Glu Asp Val Phe Ala
        915                 920                 925

Gly Lys Asn Thr Asp Leu Glu Ala Leu Met Glu Trp Leu Lys Thr Arg
        930                 935                 940

Pro Ile Leu Ser Pro Leu Thr Lys Gly Ile Leu Gly Phe Val Phe Thr
945                 950                 955                 960

Leu Thr Val Pro Ser Glu Arg Gly Leu Gln Arg Arg Arg Phe Val Gln
                965                 970                 975

Asn Ala Leu Asn Gly Asn Gly Asp Pro Asn Asn Met Asp Arg Ala Val
                980                 985                 990

Lys Leu Tyr Arg Lys Leu Lys Arg Glu Ile Thr Phe His Gly Ala Lys
        995                 1000                1005

Glu Ile Ala Leu Ser Tyr Ser Ala Gly Ala Leu Ala Ser Cys Met
        1010                1015                1020

Gly Leu Ile Tyr Asn Arg Met Gly Ala Val Thr Thr Glu Val Ala
        1025                1030                1035

Phe Gly Leu Val Cys Ala Thr Cys Glu Gln Ile Ala Asp Ser Gln
        1040                1045                1050

His Arg Ser His Arg Gln Met Val Thr Thr Thr Asn Pro Leu Ile
        1055                1060                1065

Arg His Glu Asn Arg Met Val Leu Ala Ser Thr Thr Ala Lys Ala
        1070                1075                1080

Met Glu Gln Met Ala Gly Ser Ser Glu Gln Ala Ala Glu Ala Met
        1085                1090                1095

Glu Val Ala Ser Gln Ala Arg Gln Met Val Gln Ala Met Arg Ala
        1100                1105                1110

Ile Gly Thr His Pro Ser Ser Ser Thr Gly Leu Lys Asp Asp Leu
        1115                1120                1125

Leu Glu Asn Leu Gln Ala Tyr Gln Lys Arg Met Gly Val Gln Met
        1130                1135                1140

Gln Arg Phe Lys
        1145
```

IMMUNOGEN FOR BROAD-SPECTRUM INFLUENZA VACCINE AND APPLICATION THEREOF

SEQUENCE LISTING SUBMISSION VIA EFS-WEB

A computer readable text file, entitled "SequenceListing.txt" created on Dec. 16, 2021, with a file size of 20,360 bytes contains the sequence listing for this application and is hereby incorporated by reference in its entirety.

TECHNICAL FIELD

The present disclosure relates to the research, design and production of engineered vaccines, in particular to a broad-spectrum anti-influenza virus vaccine immunogen and the uses thereof, including a novel immunogen, a recombinant vector vaccine and an immunization method thereof.

BACKGROUND

Influenza is an acute respiratory infectious disease caused by influenza virus infection, which is extremely contagious and fast-spreading. Influenza virus belongs to the Orthomyxoviridae family and is antisense single-stranded RNA virus. Seasonal influenza caused by influenza virus and frequent while unpredictable influenza pandemics have seriously endangered human health and public health. According to the World Health Organization (WHO) report statistics, 3 to 5 million people worldwide are infected with influenza A virus each year, of which there are about 250,000 to 500,000 deaths. Due to the frequent outbreaks of highly pathogenic influenza such as H5N1, H1N1, H3N2, H7N9 in recent years, it is of great significance to develop a universal influenza vaccine that has a cross-protective effect on different subtypes of influenza viruses.

The most effective and economical way to prevent influenza is vaccination. The influenza vaccines currently approved by the World Health Organization are all seasonal influenza vaccines, and most of the international research hotspots in connection with influenza vaccine are focused on inducing antibody responses against influenza virus envelope hemagglutinin protein (HA) to achieve protection. Although the HA head has a substantial immunological advantage in inducing the production of neutralizing antibody, this part is most prone to antigenic drift. Therefore, the neutralizing antibody against the HA head has strong strain specificity, and the virus will mutate selectively towards escaping neutralizing antibody, making it difficult for the antibody to achieve cross-protection. In recent years, studies have found some broad-spectrum neutralizing antibodies that target the HA rod, but they lack cross-protection against different groups of influenza viruses. Due to the subdominance of the immunogenicity of the HA rod in the natural infection state and the weak neutralizing capability against the virus, it is difficult to successfully apply such neutralizing antibodies. Studies have currently confirmed that in H7N9 influenza patients, influenza-specific CD8+ T cells have a broad-spectrum anti-influenza effect and can kill cells infected by different subtypes of influenza. Moreover, after influenza infection, influenza virus antigen-specific CD8+ memory T cells can remain in the respiratory tract for up to one year, and the number of such population of specific CD8+ cells is related to the host's cross-protection capability against influenza infection, offering a theoretical basis for the design of highly efficient and broad-spectrum antiviral influenza vaccines.

The influenza vaccines currently approved by the WHO are all seasonal influenza vaccines, among which the most widely used is the trivalent inactivated vaccine, which contains two influenza A viruses (H1N1 and H3N2) and one influenza B virus. In addition, vaccines administered subcutaneously and live attenuated vaccines administered by nasal spray are also approved for use. However, there is a common challenge for these vaccines, that is, the protective effect of the vaccine depends on the consistency between the prevailing influenza strain in that year and the vaccine strain. Influenza viruses continue to mutate, and WHO's monitoring and forecasting are time-consuming, laborious and inaccurate. In order to ensure the seasonal supply of vaccines, production must be carried out at least seven or eight months in advance, which greatly increases the uncertainty of vaccine prediction. Also, such vaccines are basically ineffective for the pandemic influenza that may occur. The current vaccine production still mainly relies on chicken embryos, with a long production cycle as well as a complicated, time-consuming, laborious and costly process. There are currently a number of strategies available for attempting to construct influenza vaccines, among which the commonly used inactivated vaccines and live attenuated vaccines lack effectiveness, with a complicated production process and a long production time.

DNA vaccines and viral vector vaccines are currently widely used. DNA vaccines have been proven to be the most effective form of primary immunization. The use of DNA vaccine for primary immunization and protein vaccine or viral vector vaccine for boosting is also the hotspot of research on immunization strategies. Currently, the most commonly used adenovirus vaccine vector is human type 5 adenovirus. Although such adenovirus is well capable of expressing foreign genes, it is easily neutralized by the pre-existing adenovirus antibodies in most human bodies due to its human origin, rendering the vaccine ineffective, and thereby limiting the use of such vaccine vector. In recent years, a gorilla-derived type 68 adenovirus vaccine vector has been discovered. There are very few antibodies against this adenovirus in the human body, which overcomes the above problems. Moreover, gorilla type 68 adenovirus can infect dividing and non-dividing cells, but also can transduce lung cells, liver cells, bone cells, blood vessels, muscles, brain, central nervous cells, etc. The type 68 adenovirus is superior in terms of gene stability and expression of foreign genes. It can be produced in large quantities with HEK293 cells and has been widely used in the research of AIDS, Ebola, influenza, malaria, hepatitis C and other vaccines. The Tiantan strain poxvirus vaccine vector has a wide host range, high reproduction titer, and a long-lasting immune response induced. Besides, the capacity for inserting foreign genes into such vector is extremely large, theoretically up to 25-50 kb. The Tiantan strain poxvirus can effectively stimulate the body to produce antibody response and T cell immune response. Due to its proven excellent safety profile, such vaccine vector can also be used by individuals with immunodeficiency.

Therefore, a severe challenge for the current broad-spectrum influenza vaccine is how to design an immunogen against the CD8 T cell epitope(s) within the influenza virus by taking advantage of the internal conserved proteins of influenza virus efficiently, and also to stimulate the immune system more comprehensively, effectively and lastingly through a variety of different vaccine vectors and their combined immunization strategies, leading to a wider range of effective protection.

SUMMARY

In one aspect of the present disclosure, there is provided an anti-influenza vaccine immunogen, wherein the immunogen comprises the amino acid sequences shown in SEQ ID No: 1 and SEQ ID No: 2 or an immunogenic fragment thereof, or a combination thereof.

In a specific embodiment of the present disclosure, the immunogen comprises internal conserved proteins of influenza virus, or immunogenic fragments of the conserved proteins.

In another specific embodiment of the present disclosure, the internal conserved proteins of influenza virus include influenza virus matrix protein (M1, M2), nucleoprotein (NP), alkaline polymerase (PB1, PB2) and acid polymerase (PA).

In another specific embodiment of the present disclosure, the immunogen is derived from recombinant proteins of all influenza virus subtypes, or recombinant proteins of shared sequences thereof, or a combination thereof and the influenza virus subtypes include H1, H2, H3, H4, H5, H6, H7, H8, H9, H10, H11, H12, H13, H14, H15, H16, H17, H18 subtypes, and type B influenza virus.

In another aspect of the present disclosure, an anti-influenza vaccine is provided, which is a recombinant vector vaccine expressed and constructed in multiple different vectors by using the above-mentioned anti-influenza vaccine immunogen or an immunogenic fragment thereof.

In a specific embodiment of the present disclosure, the recombinant vector vaccine comprises a recombinant protein vaccine, a recombinant DNA vaccine, a recombinant virus vector vaccine, a recombinant bacterial vector vaccine, a recombinant yeast vector vaccine or a recombinant virus-like particle vaccine, etc.; the virus vector comprises an adenovirus vector, a poxvirus vector, an adeno-associated virus vector, a herpes simplex virus vector, and a cytomegalovirus vector, etc.

In yet another aspect of the present disclosure, an immunization method is provided for constructing a recombinant influenza vaccine for immunization using the above-mentioned anti-influenza vaccine immunogen or an immunogenic fragment thereof, comprising the step of sequential administration with the above-mentioned different recombinant vector vaccines for each immunization, wherein each recombinant vector vaccine is administered at least once, and the vaccination process at least involves one respiratory tract administration and one systemic administration.

In a specific embodiment of the present disclosure, a recombinant vaccine derived from a different vector is used for each shot during the above-mentioned vaccination process.

In a specific embodiment of the present disclosure, the vaccination is performed by means of "primary-boost-reboost" with each recombinant vaccine administered at least once, and the vaccination process at least involves one respiratory tract administration and one systemic administration.

In a specific embodiment of the present disclosure, during the above-mentioned vaccination process, the mode of systemic administration includes intramuscular injection, subcutaneous administration, and intradermal administration; while the mode of respiratory tract administration includes atomization and nasal drop.

In a specific embodiment of the present disclosure, the above-mentioned vaccination process is as follows: primary vaccination with recombinant DNA vaccine via intramuscular injection, boosting with recombinant adenovirus vector vaccine via the respiratory tract, and reboosting with recombinant poxvirus vaccine via intramuscular injection.

In a specific embodiment of the present disclosure, the recombinant poxvirus vaccine is used as the last shot for the vaccination process.

In a specific embodiment of the present disclosure, the interval between every two shots is at least 1 week, preferably 2 weeks or more.

The vaccine and vaccination technique of the present disclosure can be used to vaccinate poultry to prevent the spread of avian influenza to human; to vaccinate human to reduce the pathogenicity of human infection with avian influenza; to vaccinate human to reduce the pathogenicity of human infection with human influenza; and also to vaccinate human to prevent human-to-human transmission of influenza.

In yet another aspect of the present disclosure, a method for treatment of tumor is provided, comprising intratumoral administration with the above-mentioned anti-influenza vaccine, wherein the tumor comprises lung cancer, liver cancer, kidney cancer, pancreatic cancer, gastric cancer, breast cancer, esophageal cancer, bladder cancer, and osteosarcoma.

In yet another aspect of the present disclosure, an immunization method is provided, wherein the above-mentioned anti-influenza vaccine is used as an adjuvant for other vaccines to enhance the immune response against other immunogens, wherein the other vaccines comprise anti-viral vaccines and anti-tumor vaccines. The other vaccines further comprise anti-ZIKV, anti-hepatitis B, anti-hepatitis C, anti-tuberculosis, anti-HIV, anti-malaria, and anti-dengue fever vaccines, etc. The other vaccines further comprise anti-lung cancer, liver cancer, kidney cancer, pancreatic cancer, gastric cancer, breast cancer, esophageal cancer, bladder cancer, and osteosarcoma vaccines.

In another aspect of the present disclosure, there is provided the use of said anti-influenza vaccine immunogen or an immunogenic fragment thereof or a combination thereof in the preparation of an anti-influenza virus vaccine.

In yet another aspect of the present disclosure, there is provided the use of said anti-influenza vaccine immunogen or an immunogenic fragment or a combination thereof as an adjuvant for other vaccines.

The present disclosure provides a broad-spectrum anti-influenza virus immunogen or an immunogenic fragment thereof or a combination thereof and an immunization method, characterized in that: the immunogen sequence comprises amino acid sequences as shown in SEQ ID No: 1 and SEQ ID No: 2, or an immunogenic fragment thereof, wherein the two sequences can be used separately or concurrently, used as a whole or in the form of a truncated immunogenic fragment, and the immunogenic fragment is equally biologically active as the sequences of the present disclosure. The immunogen sequence of the present disclosure contains influenza virus-specific CD8+ T cell epitopes that bind to human MHC class I molecule with high affinity. Recombinant vaccines have been constructed using the above-mentioned immunogen by means of a variety of different vaccine vectors. Each immunization uses different recombinant vector vaccines for sequential administration. Each recombinant vaccine is administered at least once. The vaccination process at least involves one respiratory tract administration and one systemic administration. The combination of the employed recombinant vector vaccines and administration mode can lead to a high level of T cell immune response in the respiratory tract and whole body system, such that vaccinators can obtain immunity against different subtypes of influenza.

The immunogen of the present disclosure is a recombinant protein comprising the internal conserved matrix protein (M1, M2), nucleoprotein (NP), alkaline polymerase (PB1, PB2) and acid polymerase (PA) of influenza virus, or an immunogenic fragment thereof. The immunogen sequences of the present disclosure are two sequences, named as SEQ ID No: 1 and SEQ ID No: 2 respectively.

The immunogen of the present disclosure can be used to construct recombinant vector vaccines with different vaccine vectors, including but not limited to recombinant protein vaccines, recombinant DNA vaccines, recombinant virus vector vaccines, recombinant bacterial vector vaccines, recombinant yeast vector vaccines or recombinant virus-like particle vaccines, etc.

The immunization method of the multiple recombinant vector vaccines of the present disclosure is implemented by means of "primary-boost-re-boost", that is, an immunization approach that combines systemic administration and local respiratory tract administration. Each immunization uses different vector vaccines for sequential administration. According to the characteristics of different vector vaccines, the present disclosure preferably uses the following vaccination process: primary vaccination with recombinant DNA vaccine via intramuscular injection to establish systemic immune response, then boosting with recombinant adenovirus type 68 vaccine via the respiratory tract, and finally re-boosting with recombinant poxvirus vaccine via intramuscular injection to establish systemic immune response. The present disclosure preferably uses re-boosting with recombinant poxvirus vector vaccine as the third shot, which can effectively establish a broad-spectrum influenza-specific immune response in the local respiratory tract and the whole body system, and help to enhance the broad-spectrum protection of the vaccine. The interval between every two shots is at least 1 week, and it can be 2 weeks or more.

The mode of systemic administration of the present disclosure includes, but not limited to, intramuscular injection, subcutaneous injection, and intradermal injection, etc.; while the mode of local respiratory tract administration includes, but not limited to, atomization and nasal drop, etc.

The immunogen as described in the present disclosure can be used in the research, design and production of vaccines and drugs for preventing or treating influenza virus infections in birds and mammals. In addition, the immunization method of the present disclosure can induce high-level antigen-specific CD8+ T cell responses in the local respiratory tract; as such, there is a promising prospect for preventing respiratory pathogen infection, reducing the pathogenicity of respiratory pathogens, and preventing and treating respiratory tumors.

The advantages of the present disclosure include the following: the immunogen contains highly conserved influenza CD8 T cell epitopes that bind to human MHC class I molecules with high affinity, and can induce broad-spectrum and high-level influenza-specific T cell immune response; the immunogen can effectively address influenza virus escaping the host's existing immune response due to antigen drift and antigen transformation, and has a cross-protective effect on different subtypes of influenza virus.

The advantages of the present disclosure further include the following: the immunization method adopts a variety of distinct vectors for sequential administration, and utilizes different administration modes to effectively activate the broad-spectrum T cell immune response in the respiratory tract and the whole body system, so as to enhance the vaccine's protective effect on different subtypes of influenza virus.

The advantages of the present disclosure further include the following: the immunogen and immunization method can be used for the vaccination of any respiratory pathogen vaccines; meanwhile, the recombinant vaccine prepared by the immunogen using a viral vector can be employed for the treatment of tumor via intratumor administration, including but not limited to lung cancer, liver cancer, kidney cancer, pancreatic cancer, gastric cancer, breast cancer, esophageal cancer, bladder cancer, osteosarcoma and the like.

BRIEF DESCRIPTION OF THE DRAWINGS

FIG. 1 shows the detection of immunogen expression by Western blotting. (A) shows that Western blotting has verified that the DNA vector pSV1.0, adenovirus vector AdC68 and poxvirus vector TTV all can effectively express the immunogen SEQ ID No: 1 of the present disclosure. After incubation with the influenza matrix protein 1 antibody, the empty vectors pSV1.0, AdC68, and TTV that did not contain the immunogen SEQ ID No: 1 sequence of the present disclosure showed no specific bands; while for pSV1.0-SEQ ID No: 1, AdC68-SEQ ID No: 1, TTV-SEQ ID No: 1/2 which contained the immunogen SEQ ID No: 1 of the present disclosure, a significant band with a protein size of about 130 kD can be seen, demonstrating that DNA vector pSV1.0, adenovirus vector AdC68 and poxvirus vector TTV all can effectively express the immunogen SEQ ID No: 1 of the present disclosure. Also, after incubation with β-actin antibody, a significant band with a protein size of about 42 kD can be seen, further confirming the accuracy of the experimental procedure and the reliability of the results. (B) shows that Western blotting has verified that the DNA vector pSV1.0, adenovirus vector AdC68 and poxvirus vector TTV all can effectively express the immunogen SEQ ID No: 2 of the present disclosure. After incubation with the influenza matrix protein 2 antibody, the empty vectors pSV1.0, AdC68, and TTV that did not contain the immunogen SEQ ID No: 2 sequence of the present disclosure showed no specific bands; while for pSV1.0-SEQ ID No: 2, AdC68-SEQ ID No: 2, TTV-SEQ ID No: 1/2 which contained the immunogen SEQ ID No: 2 of the present disclosure, a significant band with a protein size of about 130 kD can be seen, demonstrating that DNA vector pSV1.0, adenovirus vector AdC68 and poxvirus vector TTV all can effectively express the immunogen SEQ ID No: 2 of the present disclosure. Also, after incubation with (3-actin antibody, a significant band with a protein size of about 42 kD can be seen, further confirming the accuracy of the experimental procedure and the reliability of the results.

FIG. 2 shows the detection of the immunogen-based influenza-specific T cell immune response. (A) shows the detection of influenza-specific T cell immune response level in mouse spleen cells by enzyme-linked immunospot assay. The results showed that for the control group mice, spot-forming cells were not seen with no influenza-specific T cell immune response; for the adenovirus group mice, more spot-forming cells against the two epitopes of NP-2 and PB2-1 were seen with a higher level T cell immune response; while for the poxvirus group mice, spot-forming cells were seen against NP-2, NP-3, PB1-1, PB1-3, PA-3 and other epitopes with a higher T cell immune response. (B) shows the intracellular factor interferon gamma and tumor necrosis factor alpha staining to detect the influenza-specific immune response level in mouse spleen cells. The results showed that there were no T cells expressing interferon gamma and tumor necrosis factor alpha in the control group; while T cells expressing interferon gamma and tumor necrosis factor alpha were found in both the adenovirus group and the poxvirus group, thus demonstrating influenza-specific T cell immune response. (C) shows the intracellular factor CD107a staining to detect the influenza-specific immune response level in mouse spleen cells. The results showed that there were no CD107a-expressing T cells in the control group, and CD107a-expressing T cells were seen in the adenovirus group, thus indicating influenza-specific T cell immune response.

Figure 3:
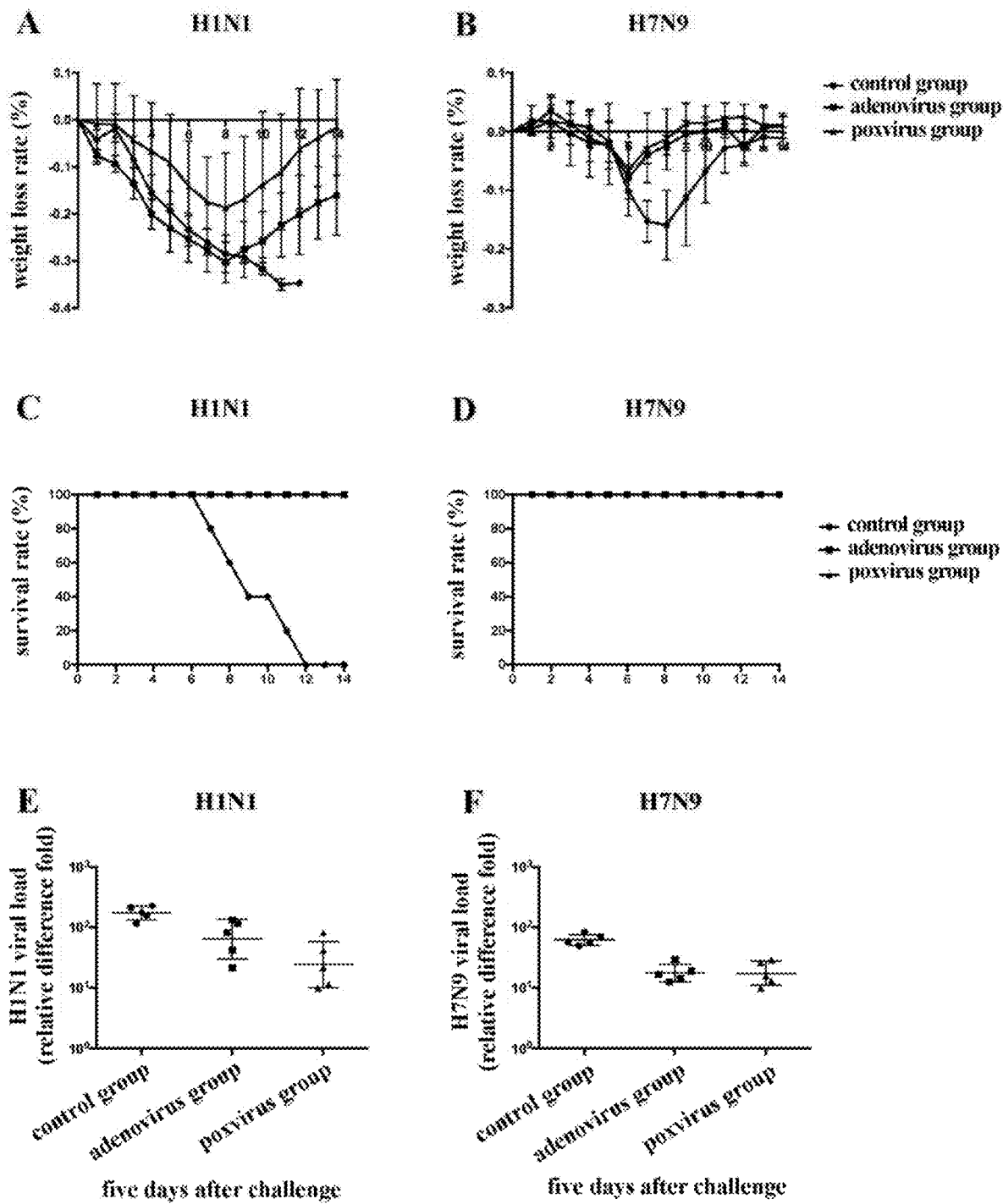

FIG. 3 shows evaluation of the protective effect of the immunogen-based H1N1 and H7N9 influenza virus challenge. (A) and (B) show the weight curve of mice. After H1N1 and H7N9 influenza virus challenge, the weight of mice in the control group continued to decrease, and the weight of mice in the adenovirus group and poxvirus group first dropped and then recovered; (C) and (D) show the survival curve of mice. After the H1N1 influenza virus challenge, all the mice in the control group died, while the mice in the adenovirus group and poxvirus group survived until 14 days; (E) and (F) show the detection of the viral load in the lungs of mice on the 5$^{th}$ day after the challenge. After the H1N1 and H7N9 influenza virus challenge, the lung viral loads of the adenovirus group and the poxvirus group were lower than those of the control group.

Figure 4:
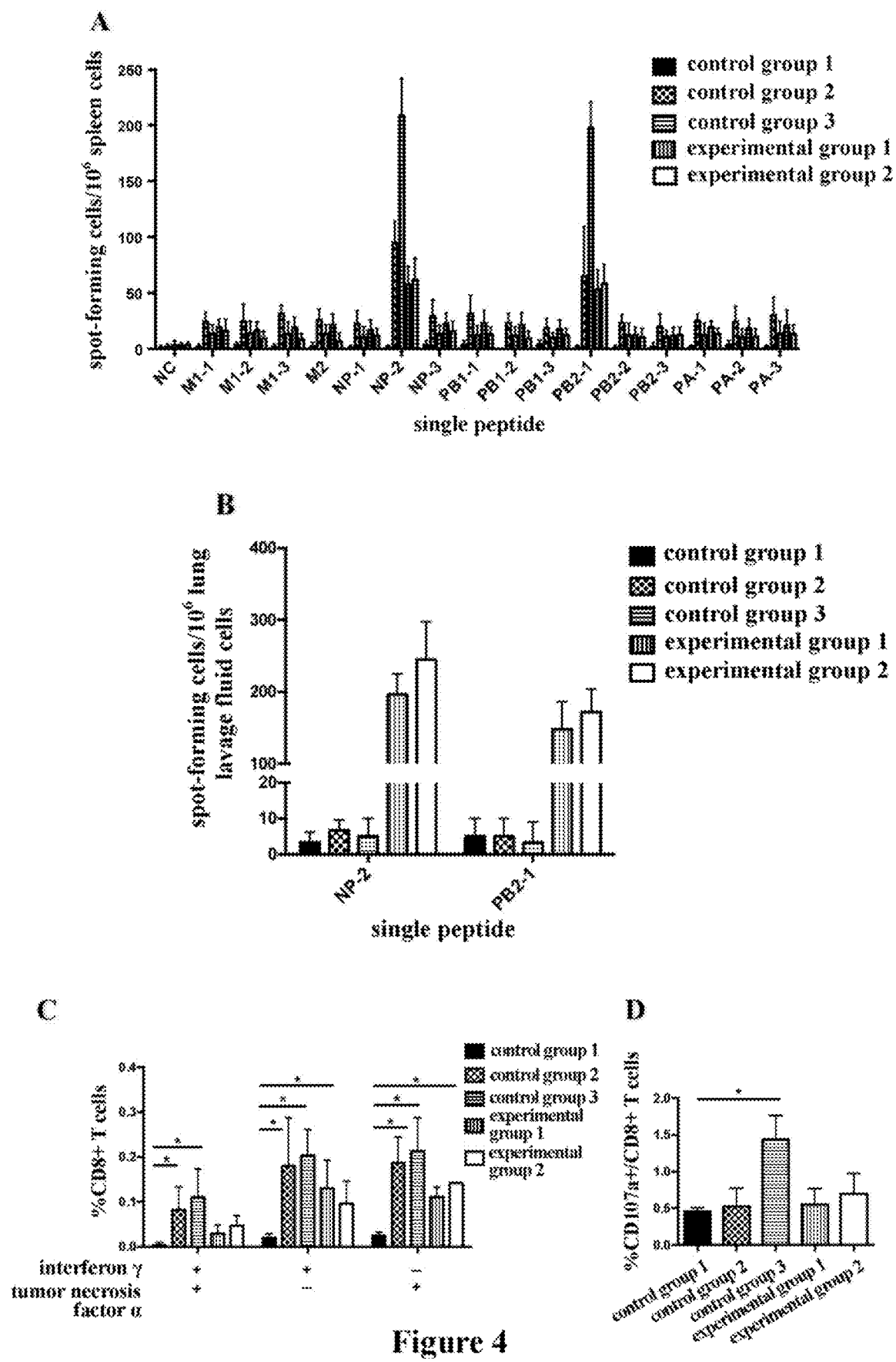

FIG. 4 shows the detection of influenza-specific T cell immune responses induced by different immunization methods. (A) shows the detection of influenza-specific T cell immune response level in mouse spleen cells by enzyme-linked immunospot assay. The results showed that for the control group mice, spot-forming cells were not seen with no influenza-specific T cell immune response; for each single peptide in the control group 2, 3 and experimental group 1 and 2, spot-forming cells were seen with a high level of T cell immune response. (B) shows the detection of influenza-specific immune response level in mouse lung lavage fluid by enzyme-linked immunospot assay. Upon stimulation by the two peptides of NP-2 and PB2-1, no spot-forming cells were seen in the control group 1, 2 and 3, and influenza-specific immune response could not be established in the lung. More spot-forming cells were seen in the experimental group 1 and 2, demonstrating a high level of influenza-specific T cell immune response; (C) shows the intracellular factor interferon gamma and tumor necrosis factor alpha staining to detect the influenza-specific immune response level in mouse spleen cells. The results showed that there were no T cells expressing interferon gamma and tumor necrosis factor alpha in control group 1, while T cells expressing interferon gamma and tumor necrosis factor alpha were found in control group 2, 3 and experimental group 1 and 2, thus exhibiting influenza-specific T cell immune response. (D) shows the detection of the influenza-specific immune response level in mouse spleen cells by intracellular factor CD107a staining. The results show that CD107a-expressing T cells can be seen in control group 3 and experimental group 2, thus indicating influenza-specific T cell immune response.

Figure 5:
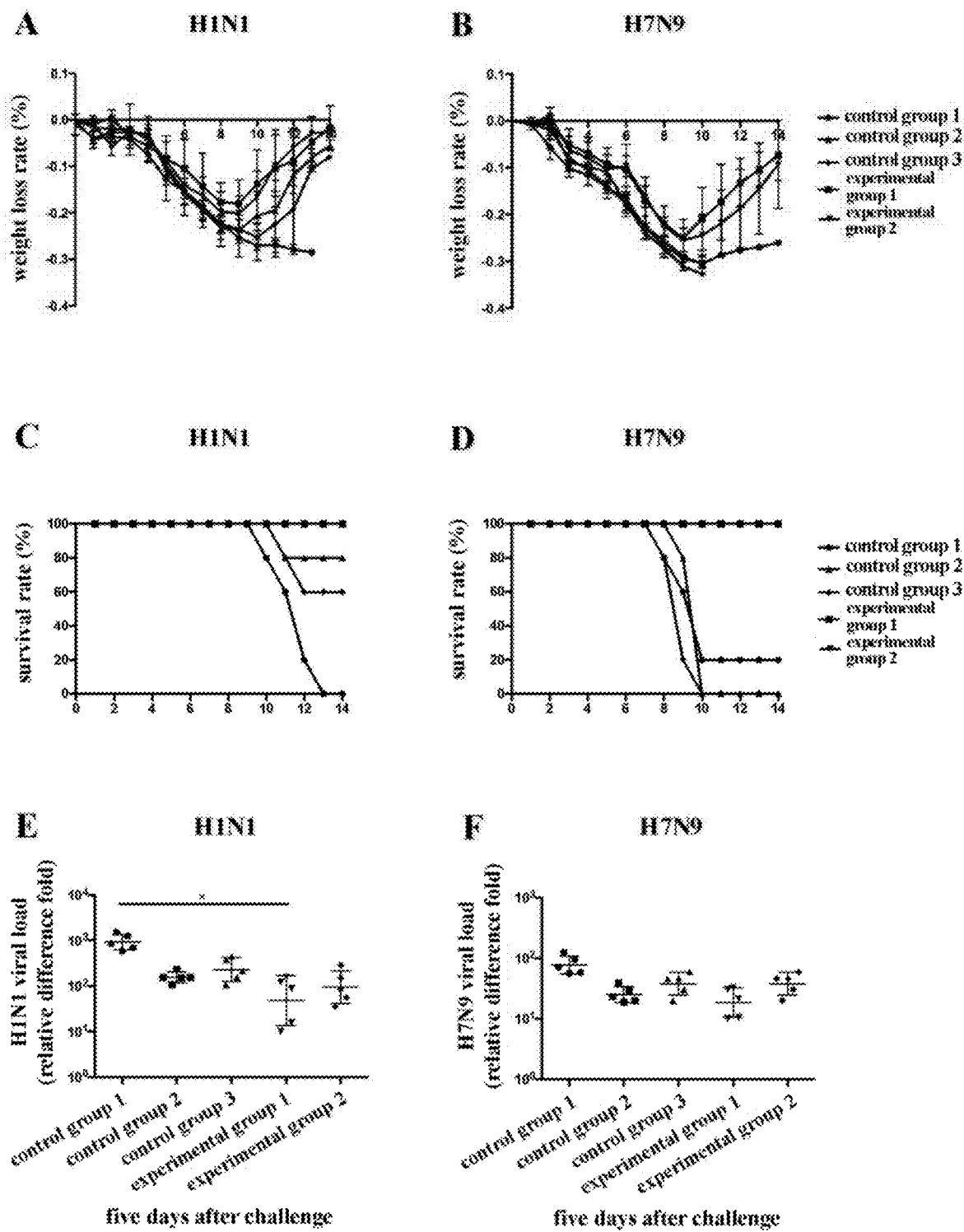

FIG. 5 shows the protective effects of mice against H1N1 and H7N9 influenza virus challenge after immunization with different methods. (A) and (B) show the weight curves of mice. After H1N1 and H7N9 influenza virus challenge, the weight of mice in the experimental group 1 and 2 mice upon H1N1 and H7N9 influenza virus infection first dropped and then recovered, which is better than the control group 1, 2, 3. (C) and (D) show the survival curves of mice. After H1N1 and H7N9 influenza virus challenge, experimental group 1 and 2 mice survived until 14 days upon H1N1 and H7N9 influenza virus infection, while death(s) was reported in each of the control group 1, 2, and 3. (E) and (F) show the virus load detection in the lungs of the mice on the 5$^{th}$ day after the challenge. After the H1N1 and H7N9 influenza virus challenge, the viral load in the experimental group 1 and 2 mice was slightly lower than that of the control group 1, 2, 3.

Figure 6:
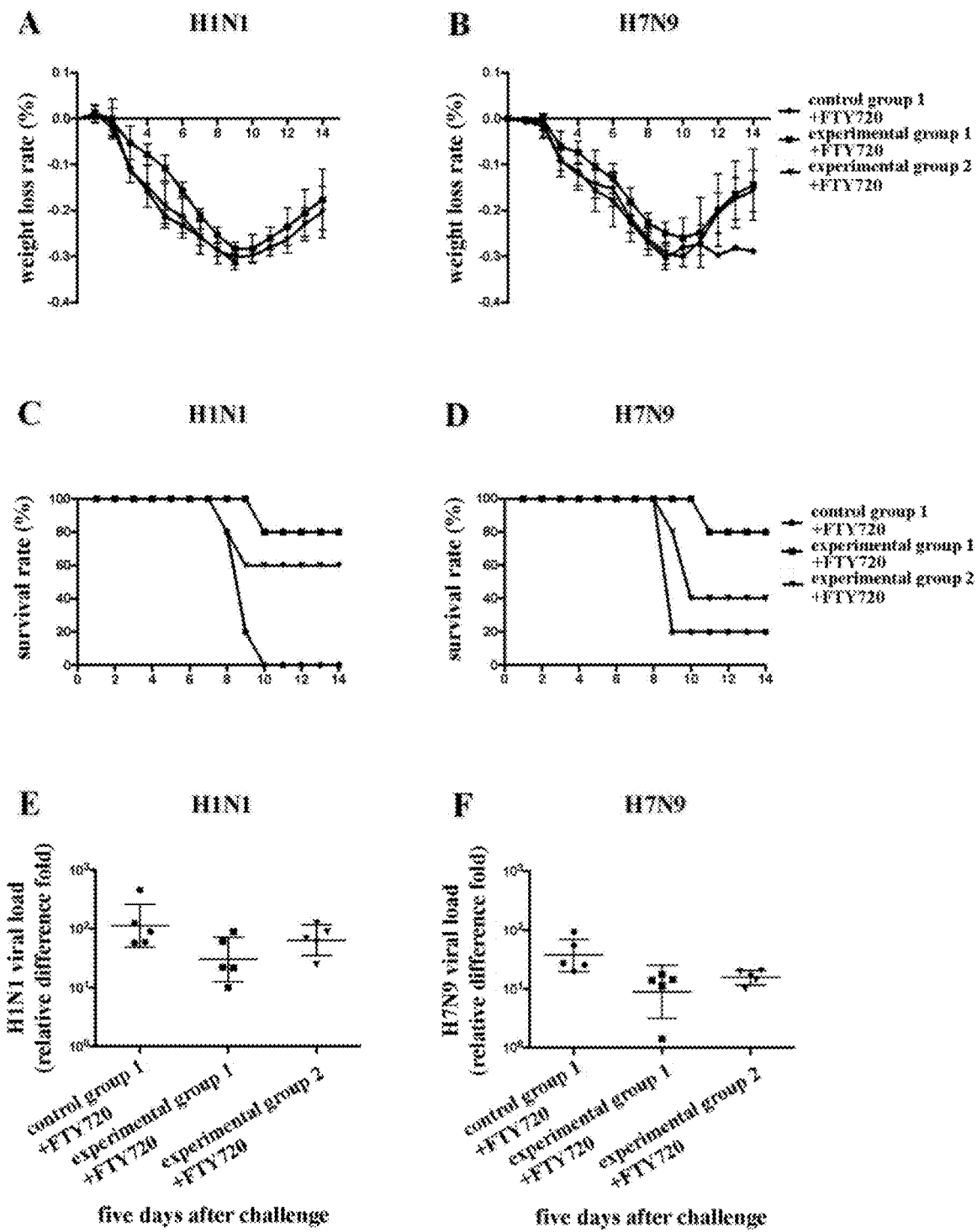

FIG. 6 shows the evaluation of the enhanced protective effect by additional nasal drop vaccination during challenge with influenza virus in the experimental group mice. (A) and (B) show the weight curves of mice. After H1N1 and H7N9 influenza virus challenge, the weight of mice in the experimental group 1+FTY720 and experimental group 2+FTY720 first dropped and then recovered, which is better than the control group 1+FTY720. (C) and (D) show the survival curves of mice. After H1N1 and H7N9 influenza virus challenge, some mice in the experimental group 1+FTY720 and experimental group 2+FTY720 survived until 14 days, which was superior to the control group+ FTY720 mice. (E) and (F) show the virus load detection in the lungs of the mice on the 5$^{th}$ day after the challenge. After the H1N1 and H7N9 influenza virus challenge, the viral load in the experimental group 1+FTY720 and experimental group 2+FTY720 mice was lower than that of the control group+FTY720.

The present disclosure will now be specifically described by way of the following examples.

DETAILED DESCRIPTION

Other aspects of the present disclosure are described in detail below. These and other features and advantages of the present disclosure will become apparent upon reading the detailed description of the embodiments disclosed below and the appended claims.

Unless otherwise defined, all technical and scientific terms used herein have the meanings commonly understood by those skilled in the art to which the present disclosure belongs.

Example 1: Design and Preparation of Anti-Influenza Vaccine Immunogen

The GenBank database is a gene sequence database established by the National Center for Biotechnology Information (NCBI), through which the gene sequences of about 40,000 strains of influenza virus can be retrieved.

The amino acid sequences of M1, M2, NP, PB1, PB2, and PA proteins interior to the above-mentioned about 40,000 strains of influenza viruses were computationally analyzed, and the amino acid with the highest frequency at each position of the amino acid sequence was regarded as the shared amino acid at that position. The shared amino acids at individual sites constitute the shared amino acid sequence of the protein, thus resulting in the shared amino acid sequences of M1, M2, NP, PB1, PB2, and PA proteins.

The online CD8 T cell epitope prediction software was used to analyze the shared amino acid sequences of PB1, PB2 and PA obtained above. The online software used is derived from tools.immuneepitope.org/main/tcell/ and www.syfpeithi.de/. The common CD8 T cell epitopes predicted by the two software programs were set aside, and then joined to form the amino acid epitope sequences of PB1, PB2 and PA.

Based on the resulting amino acid sequences above, the vaccine sequence was designed. The PA and PB1 amino acid epitope sequences obtained by epitope joining were combined with shared amino acid sequence of M1 protein to obtain an vaccine amino acid sequence, named SEQ ID No: 1. The PB2 amino acid epitope sequence obtained by epitope joining was combined with shared amino acid sequences of NP and M2 proteins to obtain an another vaccine amino acid sequence, named SEQ ID No: 2.

The above amino acid sequences SEQ ID No: 1 and SEQ ID No: 2 are translated into nucleic acid sequences, and the nucleic acid sequence is optimized for eukaryotic codon via http://www.jcat.de/ online software, resulting in the nucleic acid sequences of SEQ ID No: 1 and SEQ ID No: 2, which were synthesized by Suzhou GENEWIZ Biotechnology Co., Ltd. The synthesized sequences was sequenced by Suzhou GENEWIZ Biotechnology Co., Ltd and verified to be the sequences SEQ ID No: 1 and SEQ ID No: 2 of the present disclosure.

Example 2: Construction of Vaccine Based on Anti-Influenza Vaccine Immunogen

The immunogen of the present disclosure was used to construct a recombinant DNA vector vaccine, a recombinant adenovirus vector vaccine and a recombinant poxvirus vector vaccine.

The immunogen SEQ ID No: 1 or SEQ ID No: 2 of the present disclosure was inserted into the pSV1.0 vector (preserved by Shanghai Public Health Clinical Center) to construct a recombinant DNA vector vaccine, named pSV1.0-SEQ ID No: 1 and pSV1.0-SEQ ID No: 2 respectively.

The immunogen SEQ ID No: 1 or SEQ ID No: 2 was inserted into the AdC68 adenovirus vector (purchased from Institut Pasteur of Shanghai, Chinese Academy of Sciences) and transfected into 293a cells (purchased from the Cell Resource Center of the Shanghai Institutes for Biological Sciences, Chinese Academy of Sciences) to construct a recombinant adenovirus vector vaccine, named AdC68-SEQ ID No: 1 and AdC68-SEQ ID No: 2 respectively.

Immunogens SEQ ID No: 1 and SEQ ID No: 2 were linked using cleavage peptide p2a, inserted into pSC65 vector (preserved by Shanghai Public Health Clinical Center), and transfect into TK143 cells (purchased from the Cell Resource Center of the Shanghai Institutes for Biological Sciences, Chinese Academy of Sciences) to construct a recombinant poxvirus vector vaccine named TTV-SEQ ID No: 1/2.

The expression of anti-influenza vaccine immunogen was detected by Western blotting and the specific steps are as follows:

(1) Preparation of Experimental Samples

PSV1.0-SEQ ID No: 1 or pSV1.0-SEQ ID No: 2 was respectively transfected into 293T cells (purchased from the Cell Resource Center of Shanghai Institutes for Biological Sciences, Chinese Academy of Sciences), and 293T cells were collected 48 hours later. The collected cells were resuspended with 75 microliters of cell lysate followed by addition of 25 microliters of protein loading buffer. Samples were prepared in a water bath at 100° C. for 10 minutes.

AdC68-SEQ ID No: 1 or AdC68-SEQ ID No: 2 was respectively transfected into 293A cells, and 293A cells were collected 24 hours later. The collected cells were resuspended with 75 microliters of cell lysate followed by addition of 25 microliters of protein loading buffer. Samples were prepared in a water bath at 100° C. for 10 minutes.

TTV-SEQ ID No: 1/2 was transfected into TK143 cells, which were collected 48 hours later. The collected cells were resuspended with 75 microliters of cell lysate followed by addition of 25 microliters of protein loading buffer. Samples were prepared in a water bath at 100 degrees Celsius for 10 minutes.

(2) Western blotting: 8% polyacrylamide separation gel was prepared and left at room temperature for 30 minutes. 10% polyacrylamide concentrated gel was added immediately followed by gentle insertion of a comb. The resulting gel was left for 30 minutes until solidified, followed by loading into electrophoresis tank. The electrophoresis buffer was poured into the tank, with slow removal of the comb. The samples prepared as above were loaded sequentially. The electrophoresis was run for half an hour at 70V voltage and then at 90V for an additional 1.5 hours. After activating the polyvinylidene fluoride membrane in methanol for 30 seconds, the sponge, filter paper and polyvinylidene fluoride membrane were soaked with the transfer buffer, and were set up in sequence. The gel and ice bag were placed into the transfer tank which was then filled with the pre-cooled transfer buffer. The transfer was run at a constant current of 200 mA for 2.5 hours. Upon completion, the polyvinylidene fluoride membrane was removed and blocked in 5% skimmed milk powder for 1 hour. The influenza matrix protein 1 antibody (purchased from Abcam (Shanghai) Trading Co., Ltd.) at a dilution of 1:1000 and matrix protein 2 antibody at a dilution of 1:250 (Santa Cruz Biotechnology (Shanghai) Co., Ltd.) were added respectively. After incubating for 2 hours at room temperature on a shaker, the membrane was washed with Tween-20 in phosphate buffer for 3×5 minutes. Then, the horseradish peroxidase-labeled goat anti-mouse IgG antibody at a dilution of 1:5000 was added. After incubating for 1 hour at room temperature on a shaker, the membrane was washed with 5×5 minutes. The developer solution was prepared and then covered onto the polyvinylidene fluoride membrane for luminescence detection.

The immunogen expression results detected by Western blotting were shown in FIG. 1. The DNA vector pSV1.0, adenovirus vector AdC68 and poxvirus vector TTV all can effectively express the immunogen SEQ ID No: 1 of the present disclosure. After incubation with the influenza matrix protein 1 antibody, the empty vectors pSV1.0, AdC68, and TTV that did not contain the immunogen SEQ ID No: 1 sequence of the present disclosure showed no specific bands; while for pSV1.0-SEQ ID No: 1, AdC68-SEQ ID No: 1, TTV-SEQ ID No: 1/2 which contained the immunogen SEQ ID No: 1 of the present disclosure, a significant band with a protein size of about 130 kD can be seen, demonstrating that DNA vector pSV1.0, adenovirus vector AdC68 and poxvirus vector TTV all can effectively express the immunogen SEQ ID No: 1 of the present disclosure. After incubation with the influenza matrix protein 2 antibody, the empty vectors pSV1.0, AdC68, and TTV that did not contain the immunogen SEQ ID No: 2 sequence of the present disclosure showed no specific bands; while for pSV1.0-SEQ ID No: 2, AdC68-SEQ ID No: 2, TTV-SEQ ID No: 1/2 which contained the immunogen SEQ ID No: 2 of the present disclosure, a significant band with a protein size of about 130 kD can be seen, demonstrating that DNA vector pSV1.0, adenovirus vector AdC68 and poxvirus vector TTV all can effectively express the immunogen SEQ ID No: 2 of the present disclosure. Also, after incubation with β-actin antibody, a significant band with a protein size of about 42 kD can be seen, further confirming the accuracy of the experimental procedure and the reliability of the results.

Example 3: Detection of Immunogenicity of Anti-Influenza Vaccine Immunogen-Based Vaccine As described in Example 2, the immunogen of the present disclosure was used to construct DNA vaccines, adenovirus vector vaccines, and poxvirus vector vaccines. The recombinant influenza vaccine was used to immunize mice, and four weeks after completion of the vaccination, the immunogenicity of the recombinant influenza vaccine was evaluated.

The 6-week-old C57BL/6 mice were randomly divided into 3 groups, named control group, adenovirus group and poxvirus group. The specific vaccination procedures are shown in Table 1. The mode of administration was intramuscular injection. The administration dose was 100 micrograms for pSV1.0, $10^{11}$ virus particles for AdC68, 50 micrograms for each of pSV1.0-SEQ ID No: 1 and pSV1.0-SEQ ID No: 2, $5 \times 10^{10}$ virus particles for each of AdC68-SEQ ID No: 1 and AdC68-SEQ ID No: 2, while $10^7$ plaque forming units for TTV-SEQ ID No: 1/2. The interval between two shots was two weeks.

TABLE 1

Mouse experiment based on anti-influenza vaccine immunogen

| Group/week | 0 week | 2 weeks | 4 weeks |
|---|---|---|---|
| Control group | pSV1.0 | pSV1.0 | AdC68 |
| Adenovirus group | pSV1.0-SEQ ID No.: 1<br>pSV1.0-SEQ ID No.: 2 | pSV1.0-SEQ ID No.: 1<br>pSV1.0-SEQ ID No.: 2 | AdC68-SEQ ID No.: 1<br>AdC68-SEQ ID No.: 2 |
| Poxvirus group | pSV1.0-SEQ ID No.: 1<br>pSV1.0-SEQ ID No.: 2 | pSV1.0-SEQ ID No.: 1<br>pSV1.0-SEQ ID No.: 2 | TTV-SEQ ID No.: 1/2 |

The immunogenicity of recombinant influenza vaccines was tested in mouse spleen cells using enzyme-linked immunospot assay (ELISpot) and intracellular staining of cytokines (ICS) method.

According to the epitope prediction for SEQ ID No: 1 and SEQ ID No: 2, and the reported common influenza T cell epitopes, 16 epitope monopeptides were selected to stimulate the T cell immune response in mouse, designated as: M1-1, M1-2, M1-3, M2, NP-1, NP-2, NP-3, PB1-1, PB1-2, PB1-3, PB2-1, PB2-2, PB2-3, PA-1, PA-2, and PA-3 respectively.

(1) The Procedures for Enzyme-Linked Immunospot Assay are as Follows:

One day before the experiment, mouse interferon gamma protein was diluted to a final concentration of 5 µg/ml, added 100 µl per well to the assay plate, and coated overnight at 4° C. The next day, the coating solution was discarded. Wells were washed once with 200 microliters of complete medium for each well. Then, 200 microliters of complete medium was added for blocking at room temperature for 2 hours. Upon completion, the concentration of mouse spleen cells was adjusted to $4 \times 10^6$ cells per milliliter. Each well was added 50 microliters of spleen cells, then 50 microliters of 10 µg/ml monopeptide, for incubation in an incubator for about 20 hours. Upon completion, wells were washed twice with 200 microliters of distilled water for each well, and then washed 3 times with 200 microliters of Tween-20 in phosphate buffer. The anti-mouse interferon gamma biotin was diluted to a final concentration of 2 g/ml, added 100 microliters each well for incubation at room temperature for 2 hours. Upon completion, wells were washed 3 times with 200 microliters of Tween-20 in phosphate buffer for each well. The horseradish peroxidase fluorescent substrate was diluted 1:100, added 100 microliters each well for incubation at room temperature for 1 hour. Upon completion, each well was washed 4 times with 200 microliters of Tween-20 in phosphate buffer, and then washed twice with 200 microliters of phosphate buffer. The developer solution was prepared and added 100 microliters each well, allowing to react at room temperature for about 15 minutes in the dark. When clear red spots occurred, the plate was gently rinsed with tap water for 5 minutes to stop the chromogenic reaction. After drying at room temperature, the plate was placed into the enzyme-linked immunospot plate reader for reading and the number of positive spots was counted.

(2) The Procedures for Intracellular Factor Staining are as Follows:

The mouse spleen cells were diluted to $2 \times 10^7$ cells per milliliter. Each well was added 150 microliters of cells and 150 microliters of peptide library, then 1 microliter of CD107a antibody. After incubating for 1 hour, each well was added 0.3 microliters protein transport blocking agent for incubation in an incubator for 6 hours. Upon completion, cells were collected into a flow tube, and then centrifuged at 800 rpm for 3 minutes. The cells were washed with 800 µl staining buffer per tube and centrifuged at 800 rpm for 3 minutes. The supernatant was discarded. CD3, CD8, cell viability/cytotoxicity staining antibody mixture was prepared. Each tube was added 40 microliters of the antibody mixture and stained for 20 minutes at room temperature in the dark. Upon completion, each tube was washed twice with 800 microliters of staining buffer, centrifuged at 800 rpm for 3 minutes. The washing solution was discarded, followed by the addition of 150 microliters of fixative per tube for fixation at room temperature for 20 minutes in the dark. Each tube was washed with 800 microliters of staining buffer, centrifuged at 800 rpm for 3 minutes. The supernatant was discarded. The interferon gamma and tumor necrosis factor alpha staining antibody mixture was prepared. Each tube was added 40 microliters of the antibody mixture and stained for 20 minutes at room temperature in the dark. Each tube was washed with 800 microliters of staining buffer, centrifuged at 1200 rpm for 3 minutes. After the supernatant was discarded, the cells were resuspended in 250 microliters of staining buffer and detected by flow cytometry. Statistical results were analyzed.

Figure 2:
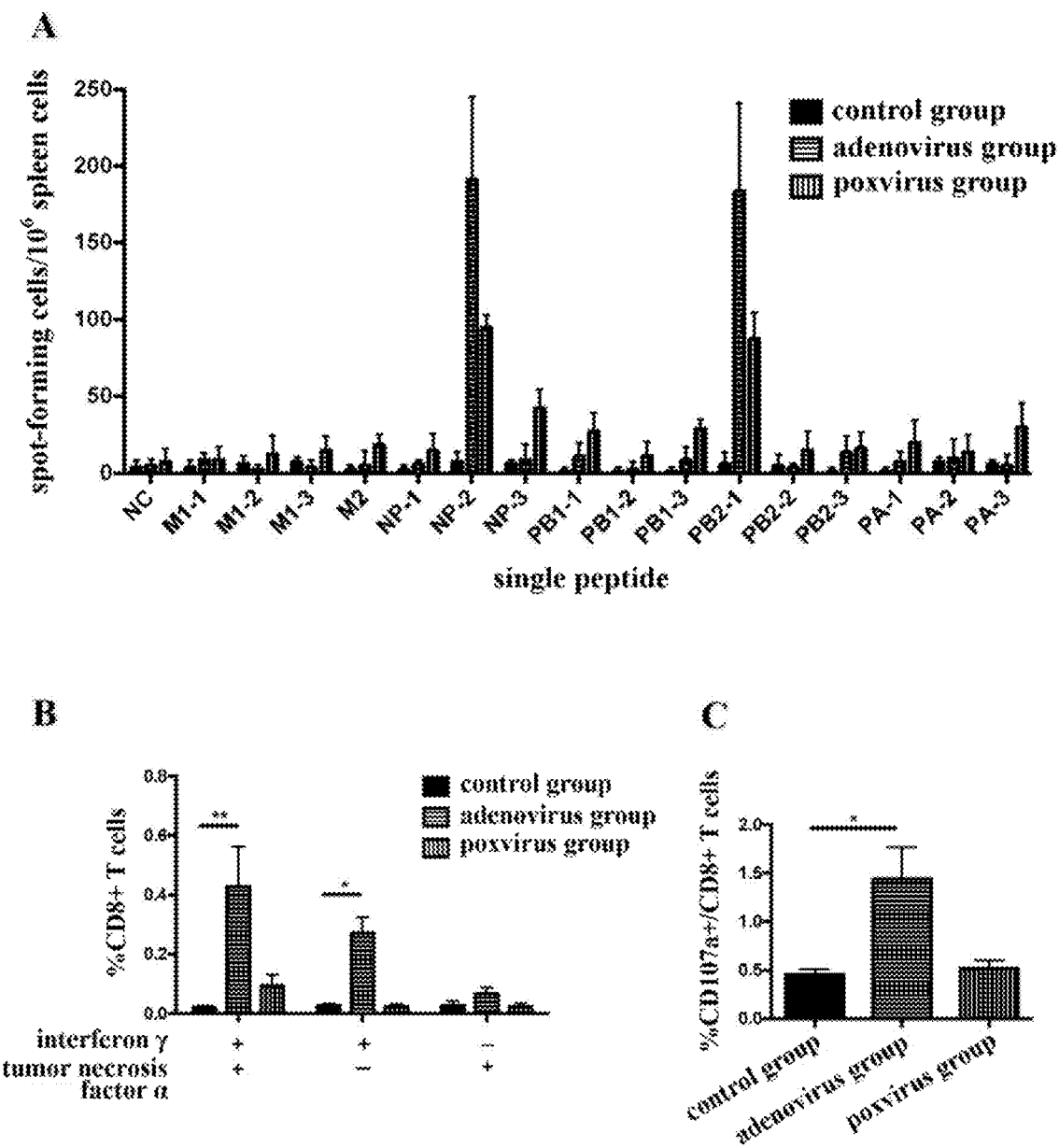

The results of the vaccine immunogenicity test are shown in FIG. 2:

The results of the enzyme-linked immunospot assay showed that for the control group mice, spot-forming cells were not seen with no influenza-specific T cell immune response; for the adenovirus group mice, more spot-forming cells against the two epitopes of NP-2 and PB2-1 were seen with a higher level T cell immune response; while for the poxvirus group mice, spot-forming cells were seen against NP-2, NP-3, PB1-1, PB1-3, PA-3 and other epitopes with a higher T cell immune response.

Intracellular factors interferon gamma, tumor necrosis factor alpha, and CD107a staining were used to detect influenza-specific immune response level in mouse spleen cells. The results showed that there were no T cells expressing interferon gamma, tumor necrosis factor alpha, and CD107a in the control group; while T cells expressing interferon gamma, tumor necrosis factor alpha, and CD107a were found in both the adenovirus group and the poxvirus group, thus demonstrating influenza-specific T cell immune response.

This Example confirmed that the expression of anti-influenza vaccine immunogens SEQ ID No: 1 and SEQ ID No: 2 through different vaccine vectors can induce significant T cell immune responses.

Example 4: Evaluation of the Challenge-Protection Based on Anti-Influenza Immunogen As described in Example 2, the immunogen of the present disclosure was used to construct DNA vaccines, adenovirus vector vaccines, and poxvirus vector vaccines. As described in Example 3, the recombinant influenza vaccine was used to immunize mice, and four weeks after completion of the vaccination, the protective effect of the recombinant influenza vaccine upon challenge was evaluated.

The H1N1 and H7N9 influenza challenge models were used to evaluate the protective effect of the immunogen. The H1N1 influenza challenge experiment was carried out in the biosafety level-2 laboratory, and the H7N9 influenza challenge experiment was carried out in the biosafety level-3 laboratory.

Each mouse was anesthetized by intraperitoneal injection of 50 microliters of 10% chloral hydrate, and each mouse was challenged with 50 microliters nasal drops of influenza virus. The challenge dose for H1N1 influenza virus was 500 $TCID_{50}$ (median tissue culture infective dose) per mouse. The challenge dose for H7N9 influenza virus was 100 $TCID_{50}$ per mouse. On the 5th day after the challenge, 5 mice in each group were sacrificed, and the lungs were taken for virus load determination.

The results of the challenge-protection results are shown in FIG. 3:

After a lethal dose challenge of H1N1 influenza virus, mice in the control group continued to lose weight and all reported death on the $12^{th}$ day. The mice in the adenovirus group began to recover on the $9^{th}$ day and all survived to 14 days. For the poxvirus group, the weight loss of the mice significantly slowed down; the body weight began to rise on the $9^{th}$ day; and all mice survived to 14 days.

After a non-lethal dose challenge of H7N9 influenza virus, mice in the control group lost nearly 20% of their body weight and recovered on the $9^{th}$ day. Mice in the adenovirus group and poxvirus group lost less than 10% of their body weight, and their body weight recovered rapidly on the $7^{th}$ day.

This Example confirmed that the expression of anti-influenza vaccine immunogens SEQ ID No: 1 and SEQ ID No: 2 through different vaccine vectors can produce cross-protective effects against H1N1 and H7N9 influenza viruses, that is, the immunogen of the present disclosure has a broad-spectrum protective effect against different subtypes of influenza virus.

Example 5: Immunogenicity Test of Influenza Vaccine Based on Different Immunization Methods As described in Example 2, the immunogen of the present disclosure was used to construct DNA vaccines, adenovirus vector vaccines, and poxvirus vector vaccines. The immunization method of the present disclosure is used to immunize mice. Four weeks after completion of the vaccination, the immunogenicity test was performed according to the method described in Example 3.

The 6-week-old C57BL/6 mice were randomly divided into 5 groups, designated as control group 1, control group 2, control group 3, experimental group 1, and experimental group 2 respectively, in which experimental group 1 and experimental group 2 adopted the immunization method of the present disclosure. The specific vaccination procedures are shown in Table 2. The administration dose was 100 micrograms for pSV1.0, $10^{11}$ virus particles for AdC68, 50 micrograms for each of pSV1.0-SEQ ID No: 1 and pSV1.0-SEQ ID No: 2, $5 \times 10^{10}$ virus particles for each of AdC68-SEQ ID No: 1 and AdC68-SEQ ID No: 2, while $10^7$ plaque forming units for TTV and TTV-SEQ ID No: 1/2. The interval between two shots was two weeks.

TABLE 2

Mouse vaccination experiment based on different immunization methods

| Group/week | 0 week | 2 weeks | 4 weeks |
|---|---|---|---|
| Control group 1 | intramuscular injection with pSV1.0 | intramuscular injection with AdC68 | intramuscular injection with TTV |
| Control group 2 | Intramuscular vaccination with pSV1.0-SEQ ID No.: 1 pSV1.0-SEQ ID No.: 2 | Intramuscular vaccination with AdC68-SEQ ID No.: 1 AdC68-SEQ ID No.: 2 | intramuscular injection with TTV-SEQ ID No.: 1/2 |
| Control group 3 | Intramuscular vaccination with pSV1.0-SEQ ID No.: 1 pSV1.0-SEQ ID No.: 2 | Intramuscular vaccination with TTV-SEQ ID No.: 1/2 | intramuscular injection with AdC68-SEQ ID No.: 1 AdC68-SEQ ID No.: 2 |
| Experimental group 1 | Intramuscular vaccination with pSV1.0-SEQ ID No.: 1 pSV1.0-SEQ ID No.: 2 | Nasal dropping of AdC68-SEQ ID No.: 1 AdC68-SEQ ID No.: 2 | Intramuscular vaccination with TTV-SEQ ID No.: 1/2 |

TABLE 2-continued

Mouse vaccination experiment based on different immunization methods

| Group/week | 0 week | 2 weeks | 4 weeks |
| --- | --- | --- | --- |
| Experimental group 2 | Intramuscular vaccination with pSV1.0-SEQ ID No.: 1 pSV1.0-SEQ ID No.: 2 | Intramuscular vaccination with TTV-SEQ ID No.: 1/2 | Nasal dropping of AdC68-SEQ ID No.: 1 AdC68-SEQ ID No.: 2 |

The results of the vaccine immunogenicity test are shown in FIG. 4:

The results of the enzyme-linked immunospot assay showed that in the spleen cells of mice, for the control group mice, spot-forming cells were not seen with no influenza-specific T cell immune response; for each single peptide in the control group 2, 3 and experimental group 1 and 2, spot-forming cells were seen with a high level of T cell immune response. In mouse lung lavage fluid, no spot-forming cells were seen in the control group 1, 2 and 3, and influenza-specific immune response could not be established in the lung; more spot-forming cells were seen in the experimental group 1 and 2, demonstrating that experimental group 1 and experimental group 2 using the vaccination method of the present disclosure showed a very high level of influenza-specific T cell immune response.

Intracellular factors interferon gamma, tumor necrosis factor alpha, and CD107a staining were used to detect influenza-specific immune response level in mouse spleen cells. The results showed that there were no T cells expressing interferon gamma and tumor necrosis factor alpha in control group 1, while T cells expressing interferon gamma and tumor necrosis factor alpha were found in control group 2, 3 and experimental group 1 and 2, thus exhibiting influenza-specific T cell immune response.

This Example confirmed that through the sequential administration of different recombinant vector vaccines, and the combination of the respiratory tract and systemic immunization, the experimental group 1 and the experimental group 2 using the vaccination method of the present disclosure can effectively establish a high level of influenza-specific immune response in both the whole body system and the local lung, which is superior to that of the control group.

Example 6: Evaluation of the Challenge-Protection Based on Different Immunization Methods According to the method described in Example 5, the immunization method of the present disclosure was used to immunize mice, and four weeks after the last shot for the mouse, H1N1 and H7N9 influenza challenge models were used to evaluate the protective effect of the immunogen. The H1N1 influenza challenge experiment was carried out in the biosafety level-2 laboratory, and the H7N9 influenza challenge experiment was carried out in the biosafety level-3 laboratory.

Each mouse was anesthetized by intraperitoneal injection of 50 microliters of 10% chloral hydrate, and each mouse was challenged with 50 microliters nasal drops of influenza virus. The challenge dose for H1N1 influenza virus was 500 $TCID_{50}$ (median tissue culture infective dose) per mouse. The challenge dose for H7N9 influenza virus was 500 $TCID_{50}$ per mouse. On the 5th day after the challenge, 5 mice in each group were sacrificed, and the lungs were taken for virus load determination.

The results of the challenge-protection results are shown in FIG. 5:

After the H1N1 influenza virus challenge, all mice in the control group 1 died on the $13^{th}$ day, while the control groups 2 and 3 showed partial protective effects, in which 80% and 60% of the mice survived to the $14^{th}$ day, respectively. The weight of mice in experimental group 1 and experimental group 2 using the vaccination method of the present disclosure recovered on the $10^{th}$ day, and all survived to the $14^{th}$ day, in which the viral load of the experimental group 2 was significantly reduced, showing an excellent protective effect.

After the H7N9 influenza virus challenge, the weight of mice in experimental group 1 and experimental group 2 using the vaccination method of the present disclosure quickly recovered on the $10^{th}$ day, and all the mice survived to the $14^{th}$ day, showing an excellent protective effect. No apparent protective effect was seen in other groups of mice.

This Example confirmed that through the sequential administration of different recombinant vector vaccines, and the combination of the respiratory tract and systemic immunization, experimental group 1 and experimental group 2 using the vaccine immunization method of the present disclosure showed excellent cross-protective effects against H1N1 and H7N9 influenza viruses; and its protective effect is superior to that of control group 2 and control group 3 which merely use one route of intramuscular injection. Moreover, when the recombinant poxvirus vector vaccine was used as the last shot of vaccine, the protective effect of the vaccine is optimal.

Example 7: Evaluation of the Enhanced Protective Effect by Additional Nasal Drop Vaccination During Challenge with Influenza Virus in the Experimental Group Mice According to the method described in Example 5, the immunization method of the present disclosure was used to immunize mice. Four weeks after the last shot for the mouse, the H1N1 and H7N9 influenza challenge models were used to evaluate the protective effect of the immunogen. The specific procedures for influenza virus attack are described in Example 6. Throughout the challenge process, the mice were continuously offered with drinking water containing 2 μg/ml FTY720. FTY720 is an immunosuppressant that can effectively reduce the number of peripheral circulating lymphocytes and retain the lung colonization of tissue in situ memory T cells established by nasal inoculation. FTY720 was continuously used during the challenge with a lethal dose of H1N1 and H7N9 influenza viruses in order to evaluate whether the nasal inoculation showed a strengthening effect.

The experimental results are shown in FIG. 6:

Upon H1N1 and H7N9 influenza virus challenge, the experimental group 1+FTY720 and the experimental group 2+FTY720 both showed partial protection. The weight of the mice began to rise on the 11$^{th}$ day and survived to the 14$^{th}$ day with a reduction in viral load. The protective effect in the experiment groups is superior to that of the control group 1+FTY720.

This Example confirmed that the administration mode via respiratory tract can effectively enhance the protective effect of the vaccine against H1N1 and H7N9 influenza.

The present disclosure is not limited to the above-mentioned embodiments, and those skilled in the art will understand that various modifications, additions, and substitutions can be made without departing from the scope and spirit of the present invention disclosed in the appended claims.

The invention claimed is:

1. An anti-influenza vaccine immunogen, wherein the immunogen comprises the sequences shown in SEQ ID No: 1 or SEQ ID No: 2, or a combination thereof.

2. The anti-influenza vaccine immunogen according to claim 1, wherein the immunogen comprises internal conserved proteins of influenza virus, or immunogenic fragments of the conserved proteins.

3. The anti-influenza vaccine immunogen according to claim 1, wherein the internal conserved proteins of influenza virus include influenza virus matrix protein (M1, M2), nucleoprotein (NP), alkaline polymerase (PB1, PB2) and acid polymerase (PA).

4. The anti-influenza vaccine immunogen according to claim 1, wherein the immunogen comprises a sequence of a protein of an influenza virus selected from the group consisting of H1, H2, H3, H4, H5, H6, H7, H8, H9, H10, H11, H12, H13, H14, H15, H16, H17, H18 subtypes, type B influenza virus, shared sequences thereof, and combinations thereof.

* * * * *